United States Patent
Hsu

(10) Patent No.: US 9,877,494 B2
(45) Date of Patent: Jan. 30, 2018

(54) ACTIVE FERMENTATION PROCESS AND FERMENTED LIQUID AND DRINKS MADE BY USING THE SAME

(71) Applicant: Shantung Hsu, Seattle, WA (US)

(72) Inventor: Shantung Hsu, Seattle, WA (US)

(*) Notice: Subject to any disclaimer, the term of this patent is extended or adjusted under 35 U.S.C. 154(b) by 211 days.

(21) Appl. No.: 14/465,780

(22) Filed: Aug. 21, 2014

(65) Prior Publication Data

US 2016/0050953 A1 Feb. 25, 2016

(51) Int. Cl.
- *A23F 3/16* (2006.01)
- *C12G 3/02* (2006.01)
- *C12N 1/20* (2006.01)

(52) U.S. Cl.
CPC .............. *A23F 3/166* (2013.01); *C12G 3/02* (2013.01); *C12N 1/20* (2013.01)

(58) Field of Classification Search
CPC .................................. A23F 3/166; C12G 3/02
See application file for complete search history.

(56) References Cited

U.S. PATENT DOCUMENTS

| | | | | |
|---|---|---|---|---|
| 3,928,140 A * | 12/1975 | Wyatt | ........................ | G01N 21/47 356/341 |
| 4,275,164 A * | 6/1981 | Masurekar | ................. | C12N 9/78 435/227 |
| 5,055,453 A * | 10/1991 | Takeuchi | ................. | C07H 15/24 435/252.1 |
| 6,254,900 B1 | 7/2001 | Hansen | | |
| 8,251,687 B2 | 8/2012 | Bertholdt | | |
| 8,444,700 B2 | 5/2013 | Bertholdt | | |
| 2005/0202122 A1 * | 9/2005 | Ichijo | ..................... | A23L 1/2006 426/52 |
| 2006/0165643 A1 * | 7/2006 | Lintner | .................. | A61K 8/645 424/74 |
| 2009/0010976 A1 | 1/2009 | Lintner | | |
| 2009/0011161 A1 | 1/2009 | Bertholdt | | |
| 2009/0214607 A1 | 8/2009 | Lintner et al. | | |
| 2010/0015283 A1 * | 1/2010 | Jung | ........................ | A23B 7/024 426/49 |
| 2010/0285176 A1 * | 11/2010 | Baek | ........................ | A23L 1/212 426/49 |
| 2011/0319607 A1 | 12/2011 | Bertholdt et al. | | |

(Continued)

FOREIGN PATENT DOCUMENTS

| CA | 2833764 A1 | 10/2012 |
|---|---|---|
| CN | 1614007 A | 5/2005 |

(Continued)

OTHER PUBLICATIONS

KR100344148B1 Jul. 22, 2002 Derwent Abstract 1 page.*

*Primary Examiner* — Felicia C Turner

(74) *Attorney, Agent, or Firm* — Mei & Mark LLP; Manni Li

(57) ABSTRACT

A process for making a fermented liquid drink comprising separating and selecting a colony of a suitable bacterial strain, preparing a seed liquid from a live culture of the colony, and culturing the seed liquid in a large scale liquid culture. The bacterial strain is of the genus of *Acetobacter* or *Gluconobacter*. The seed liquid is prepared by culturing the colony on a slant surface on a solid medium, followed by multi-stage active liquid culture. The multi-stage active liquid culture has an initial stage of small scale active liquid culture and at least one enlarged scale active liquid culture.

15 Claims, 2 Drawing Sheets

(56) References Cited

U.S. PATENT DOCUMENTS

| | | |
|---|---|---|
| 2012/0003371 A1 | 1/2012 | EkanayAke et al. |
| 2012/0039928 A1 | 2/2012 | Park et al. |
| 2013/0052148 A1 | 2/2013 | Chavan et al. |
| 2013/0171690 A1 | 7/2013 | Enders-Douglas |
| 2013/0209627 A1 | 8/2013 | MacPherson |

FOREIGN PATENT DOCUMENTS

| | | |
|---|---|---|
| CN | 100448978 C | 1/2009 |
| CN | 102440424 A | 5/2012 |
| CN | 102907532 A | 2/2013 |
| CN | 103211253 A | 7/2013 |
| CN | 103416543 A | 12/2013 |
| CN | 103416544 A | 12/2013 |
| CN | 103416545 A | 12/2013 |
| CN | 103749796 A | 4/2014 |
| DE | 102004045500 A1 | 3/2006 |
| EP | 2014182 A1 | 1/2009 |
| FR | 2865399 A1 | 7/2005 |
| JP | 3846956 B2 | 11/2006 |
| KR | 20040023982 A | 3/2004 |
| RU | 2337592 C2 | 11/2008 |
| WO | WO 9843489 A | 10/1998 |

\* cited by examiner

ACTIVE FERMENTATION PROCESS AND FERMENTED LIQUID AND DRINKS MADE BY USING THE SAME

FIELD OF THE INVENTION

The present invention relates to a process for making fermented liquid, particularly, a process based on active liquid culture for making the fermented drinks.

BACKGROUND OF THE INVENTION

Kombucha is a liquid drink with yellow-amber color and soft-acid cider taste. Kombucha is prepared by the fermentation of a tea-containing liquid by the so-called Kombucha "mushroom." The term "Kombucha" is synonymous with comboucha, cajnyj kvas (Russian), Kvass, Combuchagetränk (German), Kargasoktee (German), komboecha-drank (Dutch), Kombuchakwass (German), tea-beer, and tea-cider (English) in various culture and languages, Kombucha is believed to have antibiotic properties and nutrients including gluconic acid, vitamins $B_1$, $B_2$, $B_3$, $B_6$, $B_{12}$, folic acid, and lactic acid D(+). The health benefit of Kombucha is known and appreciated for generations in Eastern Asia, Eastern Europe, and Russia. Kombucha has been tested for the therapeutic effect in Asia and Russia and used as natural therapeutic means. In recent years, Kombucha becomes popular in the United States, and commercially produced Kombucha drinks are widely distributed throughout the country.

The Kombucha "mushroom" refers to a symbiotic mushroom-like cellulose body mainly consisting of yeast, *acetobacter, gluconobacter*, and sometimes a small amount of lactic acid bacteria *Lactobacillus bulgaricum*. The bacteria that have been isolated from Kombucha include *Acetobacter xylinum, Acetobacter xylinoides, Bacterium gluconicum, Acetobacter ketogenum, Acetobacter suboxydans, Gluconobacter liquefaciens, Acetobacter aceti*, and *Acetobacter pasteurianus*, among which *Acetobacter xylinum* is the most important. Additionally, yeasts have been isolated from Kombucha, including *Saccharomyces cerevisiae, Saccharomyces inconspicus, Saccharomycodes ludwigii, Schizosaccharomyces pombe, Candida tropicans, Candidacrusei, Debaryomyces hansenii, Brettanyomyces, Kloeckera*, and *Zygosaccharomyces bailii*.

During the conventional fermentation process for making Kombucha, one or more strains of acid bacteria and yeasts form a symbiotic relationship in the fermenting liquid. At the beginning stages of fermentation, yeasts degrade the sugar to glucose and fructose and further ferment them to ethanol, which are supplied to the acetobacters in the culture to reproduce in large quantities. Subsequently, acetobacters oxidize glucose and fructose to gluconic acid and acetic acid, and oxidize ethanol to acetic acid. Some studies show that the ethanol produced by the yeasts stimulate the growth of the acetobacters to produce more cellulose acetate membranes and acetic acid, while acetic acid in turn stimulates the yeasts to make more ethanol. The existence of acetic acid and ethanol protect the acetobacters and yeasts from being infected by other microorganisms. Additionally, the cellulose acetate membranes produced by the acetobacters form the mushroom-like body float on the top of the fermenting liquid and physically support the yeasts and bacteria to allow better exposure to the air and oxygen that are needed for the fermentation.

As the conventional fermentation process for making the Kombucha depends on the combinations of yeasts and bacteria in the culture, the taste, quality, and contents of the Kombucha vary from batch to batch. The inconsistency in the quality of the products has hindered the industrial scale production for Kombucha. Moreover, the conventional fermentation process by using the combination of yeasts and bacteria usually takes about 7 days to 2 weeks, which make the large scale production even more difficult. While the Kombucha mushroom is prod during the fermentation process and reused for making further culture, it eventually tails to make the fermented drink with the same flavor and quality within a months and needs to be constantly replenished by new cultures. Furthermore, the Kombucha may come with a strong acetic or alcohol flavor which deter some consumer from drinking and enjoying the benefits thereof.

SUMMARY OF THE INVENTION

The present invention provides a process for making a fermented liquid. The process of the present invention provides fermented liquid drinks with consistent and superior flavor and beneficial effects. The method of the present invention is safe, fast, efficient, and suitable for large scale industrial production.

The process for making a fermented liquid of the present invention comprises separating and selecting a colony of a suitable bacterial strain, preparing a seed liquid containing a live culture of the colony, and culturing the seed liquid in a large scale liquid culture to obtain a fermented liquid. The suitable bacterial strain is a species within the genus of *Acetobacter* or *Gluconobacter*. The seed liquid is prepared by culturing the colony on a slant surface on a solid medium and followed by multi-stage active liquid cultures. The multi-stage active liquid cultures have an initial stage of a small scale active liquid culture and at least one enlarged scale active liquid culture. Both the initial small scale active liquid culture and the enlarged scale active liquid culture are each conducted under an aerobic condition with continuous air ventilation and mixing for about 18 hours to about 24 hours. The seed liquid is selected from the enlarged scale active liquid culture based on the abundant and fragrant fruity taste and smell, the pH value of the culture is reduced to about 2.5 to 2.8 by the end of the culture period. Further, at the end of the enlarged scale active liquid culture, the OD640 may be about 0.15 to 0.20. The large scale liquid culture is conducted under an aerobic condition with continuous air ventilation and mixing for less than about 30 hours, wherein the pH value is at about 2.6 to 2.8 at the end of the culture period. Further, at the end of the large scale liquid culture, the OD640 of the fermented liquid reaches about 0.10 to 0.13.

In the process for making a fermented liquid of the present invention, the suitable bacterial strains are cultured and selected on the horizontal culture plate at about 28° C. to about 30° C. for about 48 to 72 hours, and the pH of the culture is about 6.0 to 6.5 for growing and selecting the colony.

The process for making a fermented liquid of the present invention may further comprise activating a preserved bacteria strain on a solid culture medium prior to selection of the colony. The solid culture medium contains vitamin Bs and is conducted on a slant surface at about 28° C. to 30° C. for about 24 to 48 hours under a starting pH of about 6.0 to 6.5.

In the process for making a fermented liquid of the present invention, the slant surface culture of the colony is conducted on a solid culture medium containing vitamin Bs at about 28° C. to 30° C. for about 48 hours under a pH of about 6.0 to 6.5.

In the process for making a fermented liquid of the present invention, the multi-stage active liquid culture for preparing the seed liquid comprises an initial stage of a small scale active liquid culture and at least one enlarged scale active liquid culture in a sequential order. The initial stage of the small scale active liquid culture is conducted in a small-scale container at about 28° C. to 30° C. under a pH of about 6.0 to 6.5, and the enlarged scale active liquid culture is conducted in a medium-scale seed liquid preparation tank in a liquid culture medium containing a tea extract at a temperature of about 28° C. to 30° C. under a pH of about 4.8 to 5.2.

In the process for making a fermented liquid of the present invention, the culture volume is enlarged about 20 times in each stage of the enlarged scale active liquid culture.

In the process for making a fermented liquid of the present invention, the large scale liquid culture is conducted at about 28 to 30° C., air ventilation rate of about 0.5 v/v/m, under a starting pH of about 4.8 to 5.2.

In the process for making a fermented liquid of the present invention, each of the enlarged scale active liquid culture and the large scale liquid culture are conducted in a liquid culture medium containing a tea extract, and may further comprise an herbal ingredient that is made from Wolfberry (*Lycium* Chinese Mill), Radix Astragali, *Ginseng*, or Hawthorn berry. In the process for making a fermented liquid of the present invention, each of the enlarged scale active liquid culture and the large scale liquid culture may also be conducted in a liquid culture medium containing an herbal ingredient that is made from Wolfberry (*Lycium* Chinese Mill), Radix Astragali, *Ginseng*, or Hawthorn berry.

In the process for making a fermented liquid of the present invention, the sugar source in culture media for each of the enlarged scale active liquid culture and the large scale liquid culture is up to about 10% volume percentage of the culture liquid, and the sugar source is glucose, sugar, honey, and optionally fruit.

The process for making a fermented drink of the present invention may further comprise a step of removing bacterial strains from the fermented liquid by filtration.

The process for making a fermented drink of the present invention may further comprise a step of optionally adjusting acidity, flavor, and texture of the fermented liquid to make the fermented drink.

Further, the present invention provides a fermented liquid and tonic beverages made by the process.

Furthermore, the process of the present invention may further comprise a step of drying the fermented liquid to make a dried substance. Moreover, the present invention provides a dietary supplement comprising the dried substance made by the process.

DETAILED DESCRIPTION OF THE INVENTION

The process of the present invention is referred to as the "active fermentation" or "active culture" process which is a unique deep layer fermentation process where the bacterial strain is carefully selected and screened through a step-by-step enlarged culture process in the flask/rotating bed, seed tank, and fermentation tank to ensure the quality and consistency in the final fermented liquid product. During the active fermentation process, the microorganism bacterial bodies are uniformly distributed in the liquid culture medium by continuous ventilation and mixing so that they may fully take up and use the dissolved nutrients in the culture medium. The entire liquid culture is a homogenous liquid culture with good thermal conductivity, in contrast to the conventional static process for making Kombucha with the mushroom-like cellulose body floating on top of the liquid. In the present invention, all the bacterial bodies fully participate in the synthesis and metabolism, thus the speed of the fermentation is faster and more efficient than the conventional method for making Kombucha. During the fermentation process of the present invention, there is no Kombucha mushroom formed on the top of the liquid, and the entire culture liquid is constantly stirred and ventilated for making the liquid.

The fermentation container may be sealed to minimize the contamination from the other bacteria. Moreover, the process is easy to operate and manage, and the process may be continuously conducted. The large scale fermentation process takes no more than 30 hours once the seed liquid is properly selected and prepared. The fermented liquid at the end contains a large amount of live culture bacteria and keeps the abundant green apple like flavor and enzyme activity.

Figure 1:
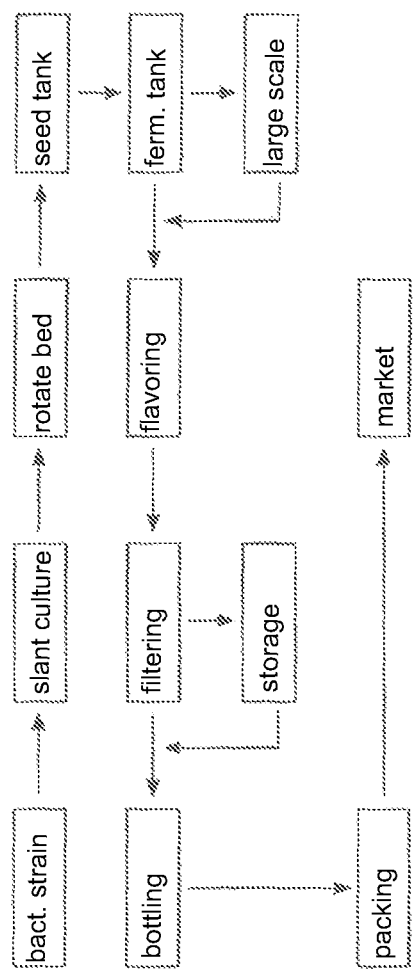
FIG. 1 is a flow chart that illustrates the general production process of the fermented drink including one embodiment of the active fermentation process of the present invention and the pre- and post-fermentation preparation and production.

As illustrated in FIG. 1, the fermentation process starts with the suitable bacterial strain. Suitable bacterial strains used in the present invention belongs to a single species from the genus of *Acetobacter* and *Gluconobacter*. The specific species mainly include *Acetobacter aceti, Acetobacter xylinum, Gluconobacter oxydans*, and *Gluconobacter cerinus*, and other species within the two genus. The suitable bacterial strain is pre-selected, separated, cultured, or treated. Preferably, the selected bacterial strain must have the characteristics of short fermentation cycle and abundant metabolite products in order to produce the fermented drinks with high nutritional value and abundant flavors. It is very important that the suitable bacterial strain is selected as the starting point of the fermentation process. Once the ideal bacterial strain is selected which is normally from a single species within the genus of *Acetobacter* and *Gluconobacter*, it is then easy to adjust and optimize the growing condition in the fermentation culture to achieve products with consistent flavor and taste.

Figure 2:
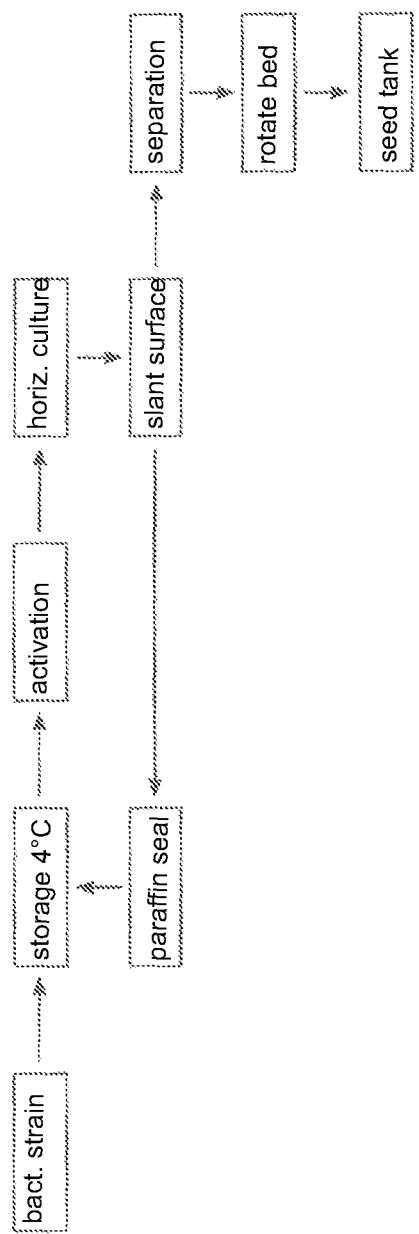
FIG. 2 is a flow chart that illustrate the preservation and activation of any preserved bacterial strain and colony for making the seed liquid of the present invention.

Preservation of the bacterial strain is known in the art. Conventional methods, including storage in the sand or clay, paraffin sealed on the slant surface medium, or storage in the glycerin have been used. Modern technological approaches also include vacuum freeze-drying and liquid nitrogen low-temperature storage. Preferably, the bacterial strain is stored in vacuum freeze-drying at −20° C., and it may last for about 4 to 5 years. As shown in FIG. 2, the bacterial strains that are used for production may be sealed by paraffin and glycerin and kept for 2 to 3 years, while the bacterial strains for the workshop production and laboratory use may be kept on the slant surface culture at 4° C. for 2 to 3 months.

As illustrated in FIG. 2, when needed, the bacterial strain in storage in the freezer may be activated. The bacteria strain is cultured on a solid culture medium on a slant surface. The solid culture medium contains vitamin Bs, and the culture is conducted at a temperature of about 28° C. to 30° C. for about 24 to 48 hours under a starting pH of about 6.0 to 6.5.

Next, a colony is selected from the activated bacterial strain or bacterial strain from any other source by culturing the bacterial strain on a horizontal plate at a temperature of about 28° C. to 30° C. for about 48 hours to 72 hours under a pH of about 6.0 to 6.5. The colonies growing on the solid culture medium are selected for further preparation. The colonies usually each contain a single species of a bacterial strain, occasionally two or more, in the genera of *Acetobacter* and *Gluconobacter*.

The process for making a fermented drink may comprise culturing the selected colonies from the horizontal plate culture on a solid culture medium on a slant surface prior to preparing the seed liquid in the multi-stage active liquid culture. The slant surface is a major means for preserving and reproducing bacterial strains over generations. The slant surface culture may be considered the starting point of preparing the seed liquid for the industrial production. The culture may be conducted on the slant surfaces in test tubes of various sizes or flask. For optimal growth and industrial production, fresh bacterial strains that have been cultured for about 24 to 48 hours are preferably used, while old bacterial strains that have been on the slant surface need to be avoided. The culture on the slant surface is conducted on the solid culture medium containing vitamin Bs at a temperature of about 28° C. to 30° C. for about 48 hours under a pH of about 6.0 to 6.5.

Subsequently, the bacterial culture on the slant surface is washed off by a sterilized water from the slant surface and added into a liquid culture in a suitable culture flask which is then placed on a rotating bed for an active liquid culture at a seeding amount of about 1 to 5%. Preferably, the flask contains 100 ml liquid culture medium and 1% volume percentage of the sterilized water containing the suitable bacterial strain is added for the initial culture. The temperature for the culture is about 28° C. to about 30° C., the speed of the rotating bed is preferably set to about 180 to 210 rpm for about 24 hours and under a pH of about 6.0 to about 6.5.

Next, through a multiple stage active liquid fermentation, a seed liquid suitable for large scale industrial production is prepared. Each of the multi-stage active liquid culture has an enlarged liquid culture volume from the previous culture, and each culture uses about 1% to 10% of liquid culture containing the bacterial strain from the previous active liquid culture. Preferably, for the initial small scale liquid culture, the seeding amount is about 1% to 5% of liquid culture from the previous liquid culture, and more preferably, 1%. In the following enlarged scale and large scale liquid cultures, preferably, about 5% of the liquid culture from the previous culture liquid is used in the next culture such that the live culture is enlarged by about 20 times in the following culture. Each of the multi-stage active liquid culture is controlled for a time period of about 24 hours or less under the aerobic condition with continuous air ventilation and mixing.

During the multi-stage active liquid culture may further comprise one or more liquid culture that are conducted successively under same culture conditions, and each of the liquid culture is conducted in an enlarged culture volume than the immediate preceding culture. For examples, the first liquid culture is conducted in a 50 ml to 100 ml liquid culture medium in a seed tank, while the second liquid culture is conducted in a 500 to 1000 ml seed tank. Both cultures are conducted at a temperature of about 28° C. to 30° C. under a pH of about 4.8 to 5.2 for about 18 to 24 hours.

The enlarged scale active liquid culture is conducted in a medium-scale seed liquid preparation tank which is important for selecting and preparing an effective seed liquid for large scale active fermentation. Fermentation tanks that are conventionally used in the pharmaceutical, food, and enzymology industries can be used for the purpose. Modern fermentation tanks are often equipped with automatic control and continuous fermentation equipment which improve the productivity and quality of the products. The enlarged scale active liquid culture comprises one or more liquid culture that are conducted successively under same culture conditions, and each of the liquid culture is conducted in an enlarged culture volume than the immediate preceding culture. The culture is conducted in a liquid culture medium containing a tea extract at a temperature of about 28° C. to 30° C. under a pH of about 4.8 to 5.2. In the stage for preparing the seed liquid, tea extract is added to the liquid culture, and effective bacterial culture are selected based on the flavor and color of the resulted liquid.

Through the continuous active liquid culture and selection, the present invention provides an effective method to screen for the most effective bacterial colony of a bacterial strains from a single species that is able to ferment within about 24 to 30 hours with abundant flavors and nutritional benefits. It is critical to select a suitable bacterial strain, followed by preparing an effective seed liquid, for the large scale production. The seed liquid must contains no other contaminating bacteria but the selected strain, has high fermentation efficiency and light yellowish color, is semitransparent, and contains abundant fruity flavor and smell. The seed liquid is prepared and taken from the end of enlarged scale active liquid culture. Preferably, the Optical Density (OD) at 640 nm of the enlarged scale active liquid culture reaches about 0.15 to 0.20 and pH reduces to a range of about 2.5 to 2.8 by the end of the culture time period. The well prepared seeding liquid shall have abundant fruity flavor and smell by the end of the enlarged scale culture.

The principle and protocol of testing the OD as an indication for the bacterial concentration in the liquid culture is known in the art. In the present invention, the OD is tested by the spectrophotometer which can be set at a wavelength of 420-660 nm. The testing wavelength must be standardized and may need to be adjusted specifically to the material being tested. Different bacterial strains may not have the same maximal absorbance wavelength. In one of the embodiments of the present invention, a wavelength at 640 nm is used for testing the OD in the present invention.

Subsequently, the large scale fermentation is conducted under the aerobic condition with continuous air ventilation and mixing, time for fermentation is controlled to less than about 30 hours, and preferably, in about 24 hours. The seed liquid that is added to the liquid culture is about 3% to 10% volume percentage of the total volume of the large scale fermentation liquid culture, and preferably, about 5% volume percentage. The large scale fermentation is conducted in a liquid culture medium containing the tea extract, the temperature for the culture is about 28 to 30° C., air ventilation rate is about 0.5 v/v/m, and the starting pH in the liquid culture is about 4.8 to 5.2. At the end of the large scale fermentation, the fermented liquid reaches a pH of about 2.6 to 2.8 and a bacterial turbidity of about 0.10 to 0.13 at OD 640. At the end of the large scale culture, the fermented liquid shall retain the abundant fruity flavor and smell of the seed liquid.

Further, the large scale fermentation may be conducted in multiple stages. For example, the large scale fermentation may be conducted in 2 stages, where the first stage is conducted in a 1 ton fermentation tank and the second stage in a 20 ton fermentation tank.

In the process for making a fermented drink of the present invention, the tea used for the manufacture of the fermented drink can be of any kind and of any origin, particularly, *Camellia sinensis*, sinensis or assamica varieties. All the varieties of green tea, semi-fermented tea, black tea, smoked black tea, yellow tea, dark tea, white tea, herb tea of plants or of fruits, infusion, can be used as the basis for manufacture of the fermented drink. Preferably, the tea extract may be prepared by green tea and water. When the bacteria are reproducing and growing in the fermentation liquid culture, the tea extract provides the benefit of trace amount of minerals and nutrients that promote bacterial growth which can't be supplied by sugar and other carbon source. The addition of the tea extract is necessary for the optimal growth of the bacteria. The tea extract is made in conventionally used industrial equipment at a ratio of about 1 g tea:25 ml water, soaking twice in water and mixing both solution so that the final ratio is about 1 g tea:50 ml water. There is no stringent requirement for the quality of the tea and tea with less quality may be used. Preferably, green tea is used. The amount of tea extract used in the seed fermentation tank is higher where 25 L tea extract is used for every 100 L liquid culture (about 500 g dried tea extract), while in the large scale fermentation tank, 10 L tea extract is used for every 100 L liquid culture (about 200 g dried tea extract).

Alternatively, tea extract may be supplemented or substituted with ingredients of herbs popular in Chinese medicine, such as Wolfberry (*Lycium* Chinese Mill), Radix Astragali, *Ginseng*, Hawthorn berry, etc., to create tonic beverages. These herbs are added in the form of water extractant or dry herbs known in the common practice.

In the culture, sugar source need to be provided as the food for the growth of the bacteria. Known sugar sources including glucose, sugar, or honey may be included in the culture. Further, various fruits may be added to provide the sugar sources. The sugar contents in the culture liquid is up to about 10% volume percentage.

Further, the process for making a fermented drink may comprise a step of removing bacterial strains from the fermented liquid by filtration. As the fermented liquid contains a large amount of bacterial colonies, these colonies contain abundant proteins that benefit the human body. However, to keep the fermented drink stably and safely stored, it is necessary to stop the post-production fermentation and stabilize the acidity of the drink. Therefore, bacteria are removed from the fermented drink so that they can be kept for one year with preserved enzyme activity and flavor. Preferably, bacteria are removed from the fermented drink by filtration under cold temperature. For example, Zeta Plus S series filters from Cuno Co. is used as the prefilter, and 0.5μ Zetapor ER filtration membrane is used for the secondary filtration to obtain bacterium-free fermented drink. After the fermented drink is filtered to remove the bacteria, it has the very light and translucent yellowish amber color and smells like fresh green apple.

Optionally, in the process for making a fermented drink of the present invention, the acidity, flavor, and texture of the fermented liquid may be adjusted to make a more flavorful fermented drink. The fermentation process depends on the reproduction and metabolism of the microorganisms. During the manufacture of the fermented drink, despite the tight control of the production parameters, the product may have variations as opposed to chemically mixed drinks with uniform contents. In order to have consistent drink product, the fermented drink may be mixed and adjusted for flavor, texture, and acidity. The drink products from different batches or fermentation tanks may be mixed, and the sweetness, acidity, concentration, and flavor may be further adjusted in accordance to consumer taste. The acidity may be adjusted slightly at a dilution of 2% to maintain the delicate flavor and fragrance of the drink. If strong flavor is desired, certain natural flavoring additive may be added, such as natural strawberry flavoring agent, to please the consumer. No matter what measures are taken to mix and adjust the final drink products, the products are always based on the naturally brewed and fermented drink, unlike most of the commercially available drinks which completely depend on the mixture of artificial ingredients. Further, the fermented drink may be aged like wine. After a prolonged period of time, the fermented drink may gain more abundant flavor and with even higher quality and taste.

The present invention further provides a fermented liquid, seed liquid, and fermented drink made by the processes of present invention. The fermented drink may be dried to make a dry substance and added or used for various dietary supplement. In the fermented drink as prepared by the process of the present invention, the taste, flavor, and nutrient value are superior to any drinks available on the current market. During the fermentation and reproduction process, the microorganisms produce large quantities of metabolites, including amino acids, vitamins, organic acids, and enzymes, which are beneficial to human body while retaining plentiful flavor and taste.

The present invention is further illustrated in the following examples. The examples do not limit the scope of the present invention, as one of skilled in the art may modify the examples without departing from the scope of the present invention.

Example 1. Activation of Bacterial Strain

Starting bacterial strain or bacterial strain that has been preserved in the fridge or freeze-drying need to be activated prior to further culture and selection of single colonies. A solid culture medium is prepared on a slant surface by dissolving 20.0 g glucose, 10.0 g yeast powder, 3.0 g beef extract, 10.0 g $CaCO_3$, 20 mg Vitamin Bs mixture, and 20.0 g agar in 1000 ml water at natural pH of 6.0 to 6.5 in a large container in a heated condition; pouring 4 ml to 5 ml dissolved solution into each 25 ml small test tube; sealing the test tubes with cotton seals and pasteurizing for 30 minutes at 120° C.; placing the test tubes at an angle while hot so that the slant surface of the solid culture medium is formed on the top. The bacterial strain is seeded on the slant surface by seeding loop, and cultured at a thermo-incubator at 28° C. to 30° C. for 24 to 48 hours.

Example 2. Purification and Selection of Single Colony

The solid culture medium is prepared on a horizontal surface by dissolving 20.0 g glucose, 10.0 g yeast powder, 3.0 g beef extract, 10.0 g $CaCO_3$, 20 mg Vitamin Bs mixture, and 20.0 g agar in 1000 ml water at natural pH of 6.0 to 6.5 in a large container; pouring 200 ml dissolved solution into each 500 ml flask; sealing the flasks with cotton seals and pasteurizing for 30 minutes; cooling the pasteurized solution to 50° C. to 60° C., and pouring 20 ml solution onto each horizontal plate having a diameter of 9 cm to cool down and form the solid horizontal plate culture medium.

Next, a few bacterial colonies from the activated bacterial culture in Example 1 are picked by seeding loop and seeded on the horizontal plate by drawing separated lines. The horizontal plates are cultured at an incubator at 28° C. to 30°

C. for 48 to 72 hours. Single colonies are grown on the solid culture and picked out for further preparation.

Example 3. Slant Surface Culture of Single Colonies

The single colonies of live culture from Example 2 are further cultured on the slant surface. Single colonies grown on the horizontal plate are selected by seeding loop and seeded on the slant surface prepared as in Example 1. Single colonies that have bigger transparent circle around are the healthy colonies and preferred. As the bacteria grow and produce acid, the acid reacts with $CaCO_3$ in the medium; as the amount of $CaCO_3$ reduced, the transparent circle forms around the colony, which indicates healthy growth.

Each single colony is seeded on 2 to 3 slant surface culture, and the test tubes are cultured at an incubator at 28° C. to 30° C. for about 48 hours. Single colonies that grow well with no contamination are kept in the fridge for further preparation.

Example 4. Multi-Stage Rotating Bed Liquid Culture

Liquid culture medium is prepared by dissolving 20.0 g glucose, 10.0 g yeast powder, 3.0 g beef extract, 1.0 g $KH_2PO_3$ in 1000 ml water at natural pH of 6.0 to 6.5 in container; pouring 100 ml dissolved solution into each 500 ml triangular flask; sealing the flasks with cotton seals and pasteurizing for 30 minutes at 120° C. The liquid culture medium is prepared when cooled down. Bacterial colonies from the slant surface culture of Example 3 are washed with 5 ml sterile water and seeded into the 100 ml liquid culture medium in a 500 ml triangular flask. The culture is conducted at 28° C. to 30° C. for about 24 hours on a rotating bed with a rotation speed of 180 rpm to 210 rpm.

Next, 1% liquid culture from the previous culture in the 500 ml triangular flask is seeded into 200 ml liquid culture medium in a 1000 ml triangular flask. The culture medium is the same as prepared above except with enlarged proportions and volume. The culture is conducted at 28° C. to 30° C. for about 24 hours on a rotating bed with a rotation speed of 180 rpm to 210 rpm to obtain a live culture suitable for preparing a seed liquid.

Example 5. Seed Tank Liquid Culture Fermentation

Liquid culture medium is prepared by dissolving 3.0 kg glucose and 6.0 kg sugar in 75 kg sterile water in the autoclaved fermentation tank. The tank is heated to 100° C. and maintained at the temperature for 15 minutes. When the temperature is let to cool down, 25 kg tea extract and 900 ml food-grade ethanol are added to the tank. Then, the live liquid culture 1% volume percentage from Example 4 is added into the tank. The pH value in the liquid culture is adjusted to 5.0±0.2 by adding NaOH. The culture is conducted at 28° C. to 30° C. for about 18 to 24 hours on a rotating bed with a rotation speed of 57 rpm. The culture is conducted under air ventilation and the minute ventilation rate is about 0.5 air volume/culture volume/minute (v/v/m). At the end of the stage, the bacterial turbidity OD value is about 0.150 to 0.200, pH value is reduced to about 2.5 to 2.8, fruity flavor and abundant taste can be tasted. Then, the seed liquid is ready.

Example 6. Large Scale Fermentation Culture

Liquid culture medium is prepared by dissolving 1.0 kg glucose and 11.0 kg sugar in 80 kg sterile water in the autoclaved fermentation tank. The tank is heated to 100° C. and maintained at the temperature for 15 minutes. When the temperature is let to cool down, 10 kg tea extract and 450 ml food-grade ethanol are added to the tank. Then, the seed liquid is added at 5% volume percentage from Example 5. The pH value in the liquid culture is adjusted to 5.0 by adding NaOH. The culture is conducted at 28° C. to 30° C. for 24 hours while stirring. The culture is conducted under air ventilation and the minute ventilation rate is about 0.5 v/v/m. At the end of the fermentation, the bacterial turbidity OD value at OD640 is about 0.10 to 0.13, pH value is reduced to about 2.6 to 2.8, fruity flavor and abundant taste can be tasted with light yellowish semitransparent color. The fermented liquid drink is prepared.

I claim:

1. A process for making a tea-based fermented drink for human consumption, comprising
   preparing a colony consisting of a bacterial strain, wherein the bacterial strain is from a single species selected from the group consisting of *Acetobacter aceti*, *Acetobacter xylinum*, *Gluconobacter oxydans*, and *Gluconobacter cerinus*,
   preparing and selecting a seed liquid from culturing the colony through sequentially a slant surface culture, an initial small scale active liquid culture, and at least one enlarged scale active liquid culture, wherein the seed liquid consists of a culture of the colony of the single species without any contaminating bacteria, and
   culturing the seed liquid in a large scale active liquid culture to obtain the tea-based fermented drink,
   wherein the slant surface culture is conducted at a pH of about 6.0 to 6.5 for about 48 hours;
   the initial small scale active liquid culture is conducted at a pH of about 6.0 to 6.5 under an aerobic condition with continuous air ventilation and mixing to uniformly distribute bacteria in the culture liquid for about 18 to 24 hours;
   the enlarged scale active liquid culture is conducted under an aerobic condition with continuous air ventilation and mixing to uniformly distributing bacteria in the culture liquid for about 18 to 24 hours under a starting pH of about 4.8 to 5.2 and in presence of a tea extract at 25% volume of the culture liquid;
   the seed liquid is selected at the end of the enlarged scale active liquid culture, wherein the seed liquid has the pH of the culture liquid reduced to about 2.5 to 2.8, an OD at 640 nm at about 0.150 to 0.200 and yellowish color and fruity flavor within the about 18 to 24 hours for the enlarged scale active liquid culture; and
   the large scale active liquid culture is conducted under an aerobic condition with continuous air ventilation and mixing to uniformly distribute bacteria under a starting pH of about 4.8 to 5.2 and in presence of a tea extract at 10% volume of the culture liquid for less than about 30 hours and having the pH reduced to about 2.6 to 2.8 and an OD at 640 nm at about 0.10 to 0.13 within the less than about 30 hours for the large scale active liquid culture to obtain the tea-based fermented drink.

2. The process for making a tea-based fermented drink as described in claim 1, wherein the colony is prepared by a horizontal culture at about 28° C. to 30° C. for about 48 to 72 hours under a pH of about 6.0 to 6.5.

3. The process for making a tea-based fermented drink as described in claim 1, further comprising
   activating a preserved bacteria strain on a solid culture medium prior to preparing the single colony, wherein the solid culture medium contains vitamin Bs, and the culture is conducted on a slant surface at about 28° C. to 30° C. for about 24 to 48 hours under a starting pH of about 6.0 to 6.5.

4. The process for making a tea-based fermented drink as described in claim 1, wherein the enlarged scale active liquid culture is conducted in a medium-scale seed liquid preparation tank in a liquid culture medium.

5. The process for making a tea-based fermented drink as described in claim 4, wherein the enlarged scale active liquid culture comprises two or more active liquid cultures and culture volume of each enlarged scale active liquid culture is enlarged about 20 times from a previous enlarged scale active liquid culture.

6. The process for making a tea-based fermented drink as described in claim 1, wherein the large scale liquid culture is conducted at about 28 to 30° C., and the air ventilation rate of about 0.5 v/v/m.

7. The process for making a tea-based fermented drink as described in claim 1, wherein the liquid culture medium further comprises an herbal ingredient that is made from Wolfberry (*Lycium* Chinese Mill), Radix Astragali, *Ginseng*, or Hawthorn berry.

8. The process for making a tea-based fermented drink as described in claim 1, wherein each of the enlarged scale active liquid culture and the large scale liquid culture are conducted in a liquid culture medium containing an herbal ingredient that is made from Wolfberry (*Lycium* Chinese Mill), Radix Astragali, *Ginseng*, or Hawthorn berry.

9. The process for making a tea-based fermented drink as described in claim 1, wherein sugar source in culture media for each of the enlarged scale active liquid culture and the large scale liquid culture is up to about 10% volume percentage of the culture liquid, and the sugar source is glucose, sugar, honey, and optionally fruit.

10. The process for making a tea-based fermented drink as described in claim 1, further comprising
removing bacterial strains from the fermented drink by filtration.

11. The process for making a tea-based fermented drink as described in claim 10, further comprising
optionally adjusting acidity, flavor, and texture of the fermented drink to make the fermented drink.

12. A tea-based fermented drink made by the process of claim 1.

13. A tea-based fermented drink made by the process of claim 8.

14. The process for making a tea-based fermented drink as described in claim 1, further comprising
drying the fermented drink to make a dried substance.

15. Dietary supplement comprising the dried substance made by the process of claim 14.

* * * * *